United States Patent

Shirouzu et al.

[11] Patent Number: 5,891,070
[45] Date of Patent: Apr. 6, 1999

[54] BREAST PRESSER BELT

[75] Inventors: Toshimichi Shirouzu, Akashi; Takefumi Nakashita, Kobe, both of Japan

[73] Assignee: Sumitomo Rubber Industries, Ltd., Kobe, Japan

[21] Appl. No.: 744,074

[22] Filed: Nov. 4, 1996

[30] Foreign Application Priority Data

Nov. 9, 1995 [JP] Japan .................................. 7-290968

[51] Int. Cl.$^6$ ...................................................... A61F 5/00
[52] U.S. Cl. .................................................. 602/19; 602/13
[58] Field of Search ................................. 602/4, 20, 19, 602/53, 63, 65, 74, 13; 128/96.1, 99.1–102.1, 106.1, 112.1, 869

[56] References Cited

U.S. PATENT DOCUMENTS 3,245,406  4/1966  Chardack ................................. 602/79
5,188,587  2/1993  McGuire et al. ....................... 602/4 X
5,423,852  6/1995  Daneshvar ............................. 606/201

*Primary Examiner*—Richard J. Apley
*Assistant Examiner*—Kim M. Lee
*Attorney, Agent, or Firm*—Nikaido, Marmelstein, Murray & Oram LLP

[57] ABSTRACT

A breast presser belt 1 comprising a belt body 2 adapted to be removably wrapped around a breast portion of a user, a presser member 3 adapted to extend from the belt body 2 over to the breast portion of a user, and a bag 4 adapted to be inflated by means of an appropriate fluid. The bag 4 is attached to the inner surface of the presser member 3 at a predetermined position. When the bag 4 is inflated, the breast presser belt 1 pressurizes the breast portion of a user and securely fastened to the breast portion. Thus, the pressurizing location of the breast presser belt 1 is prevented from being shifted. The breast presser belt does not require a user or patient to keep still on a bed. Allergic poisoning, previously experienced due to the use of medical adhesive tape, may be obviated. The breast presser belt may be applied to a female having larger breasts.

3 Claims, 4 Drawing Sheets

BREAST PRESSER BELT

FIELD OF THE INVENTION

This invention relates to a breast presser belt suitable for use in pressing a wound through which a the cardiac pacemaker is implanted, after cardiac implantation operation.

BACKGROUND OF INVENTION

Recently, a pacemaker implantation operation has been performed relative to a cardiopath. The pacemaker includes an electrode attached to a heart of a patient. The electrode gives an electric pulse periodically to the heart, so as to activate contraction ability of the heart.

The pacemaker is implanted into a body of a patient through an incision in a breast portion of the patient. After implantation, the incision should be sutured and pressed or compressed for a relatively extended period of time until the wound becomes completely healed, so as to maintain the pacemaker at a fixed position. By this, tissue growth at the wound, which otherwise would be obstructed by displacement or shifting of the pacemaker, may be facilitated.

In a conventional way for pressing or compressing an incision for a relatively long period of time after completion of pacemaker implantation operation, a piece of gauze is applied to the incision and fixed thereby means of medical adhesion tape. Then, a weight adjusted to 500 gr. to 1 kg., such as a sand bag, is placed on the medical adhesive tape so as to immobilize the same. The immobilized or fixed condition of the medical adhesive tape is maintained for a relatively long period of time.

According to a prior art method mentioned above, fixation or immobilizaton of the weight such as a sand bag is not sufficienty achieved. Displacement of the pacemaker is easily caused due to shifting or displacement of the weight, whereby tissue growth is disadvantageously delayed. It is also noted that, since pressing force or compressing force from the weight is only exerted in the direction of gravity, a patient is required to keep still on a bed for a relatively long time of period. In such a situation, the patient is prevented from turning in bed. Since medical adhesive tape is used as a means for fixing the gauze and the weight, allergic poisoning can be caused to a patient. Furthermore, the weight cannot be easily applied to a female patient having larger breasts.

SUMMARY OF THE INVENTION

In view of the above problems in prior art, the invention is aimed at provision of a breast presser belt which is not easily shifted or displaced so as to facilitate tissue growth around the wound, which does not require a user or patient to keep still in bed, which obviates allergic poisoning previously caused by the use of medical adhesive tape, and which may be applied to a female patient having larger breasts.

In order to achieve the above object, the present invention provides a breast presser belt which comprises a belt body adapted to be removably wrapped around a breast portion of a user, a presser member adapted to be extend from the belt body over to the breast portion, and a bag attached to the inner surface of the presser member at a predetermined position and being inflatable by means of an appropriate fluid.

A second invention is featured by that the presser member is a shoulder belt which is adapted to pass over a shoulder portion of a user so as to connect together the breast-side portion and the back-side portion of the belt body.

A third invention is featured by that the presser member is a hard plate member of an inversed T-shaped configuration, the hard plate member being formed from a hard material.

A fourth invention is featured by that a reinforcing member is disposed around the bag for restricting the direction of inflation of the bag solely toward the breast portion of a user.

A fifth invention is featured by that an arm fixing belt is attached to the belt body at a predetermined position.

BRIEF DESCRIPTION OF THE DRAWINGS

For a fuller understanding of the nature and objects of the present invention, reference should be had to the following detailed description taken in connection with the accompanying drawings wherein.

DETAILED DESCRIPTION OF THE PREFERRED EMBODIMENTS

Figure 1:
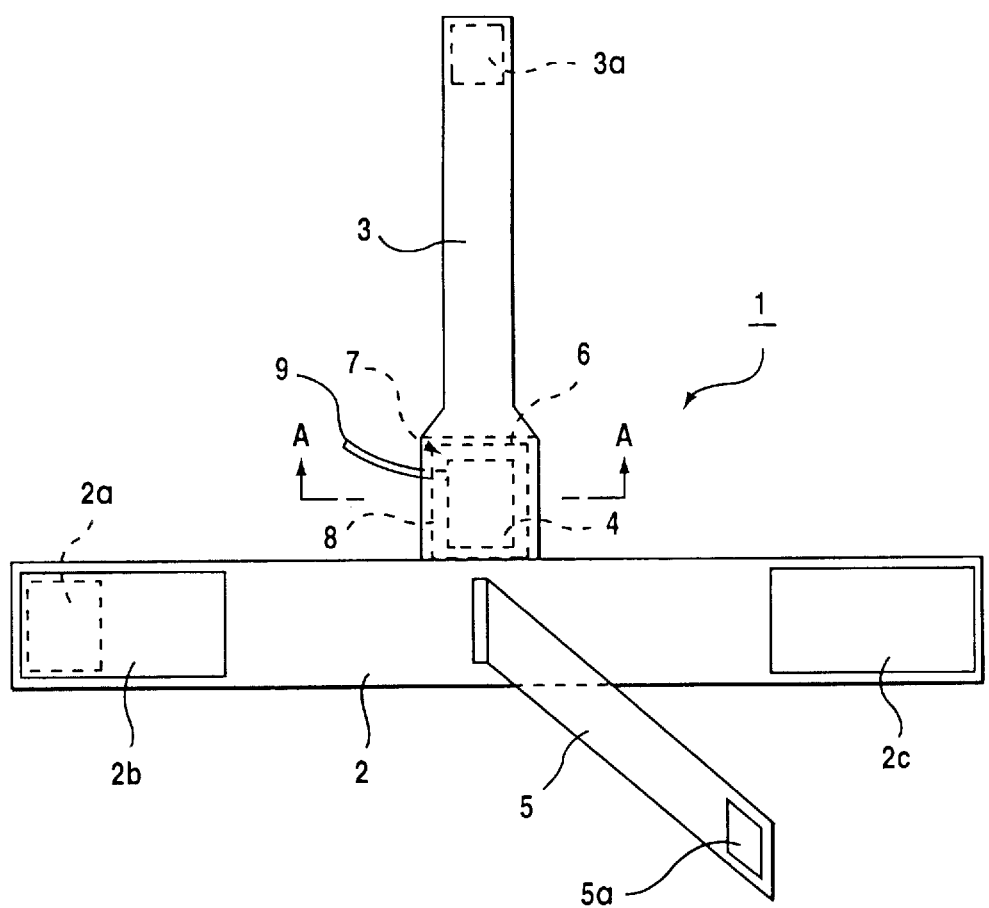
FIG. 1 is a front elevational view showing a breast presser belt according to one embodiment of the invention.
Figure 2:
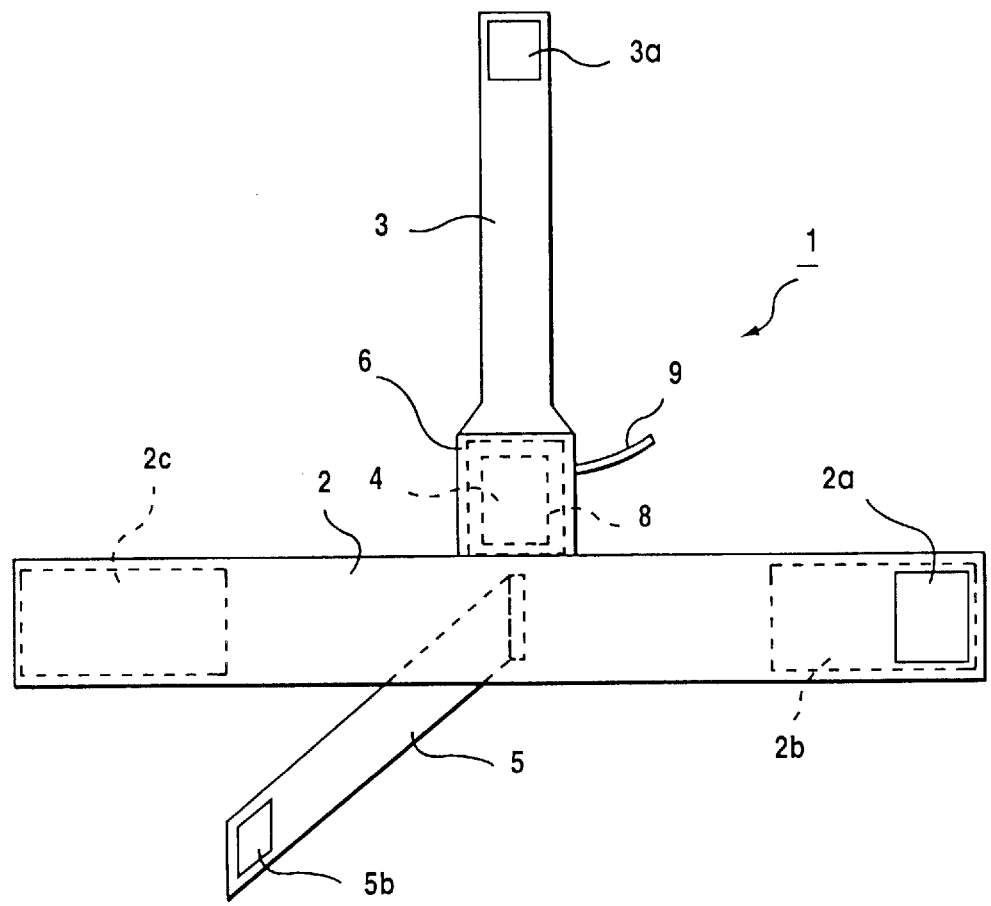
FIG. 2 is a rear elevational view showing the breast presser belt according to the embodiment of the invention.
Figure 3:
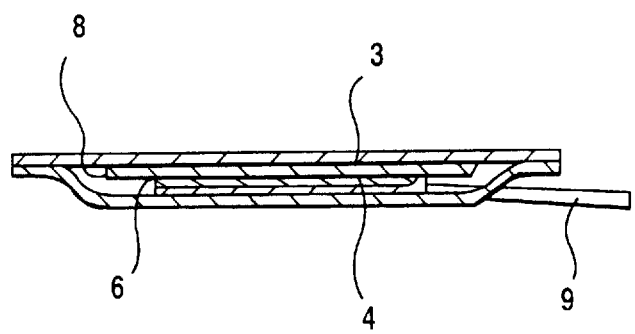
FIG. 3 is an enlarged cross-sectional view along line A—A of FIG. 1.

FIGS. 1 to 3 show a breast presser belt according to one embodiment of the invention. The breast presser belt 1 includes a belt body 2 of an elastic or non-elastic material adapted to be removably attached to a breast portion of a user, a shoulder belt 3 of an elastic or non-elastic material secured to the belt body 2 at a predetermined position, the shoulder belt 3 serving as a presser member, and a bag 4 attached to the shoulder belt 3 at a predetermined position in its inner surface, the bag 4 being adapted to be inflated by a suitable fluid.

The belt body 2 is formed from an elastic or non-elastic material. It is noted, however, that the belt body may preferably be formed from a mesh fabric, such as nylon, having a superior gas permeability. A hook-and-loop fastener 2a, as a securing means, is fixed, for example, by means of sewing or adhesive, to the inner surface of one end portion (left-hand end-portion in FIG. 1) of the belt body 2. Similarly, hook-and-loop fasteners 2b and 2c, as securing means, are fixed, for example, by means of sewing or adhesive, to the outer surface of the opposite end portions of the belt body 2. An arm fixing belt 5 of an elastic or non-elastic material is sewn on the belt body 2 at a predetermined position on the outer surface thereof, and extends outwardly therefrom. Hook-and-loop fasteners 5a and 5b, as securing means, are fixed, for example, by means of sewing or adhesive, respectively to the opposite side surfaces of the forward end portion of the arm fixing belt 5.

The shoulder belt 3 is formed from an elastic or non-elastic material. It is noted, however, that the shoulder belt 3 may preferably be formed from a mesh fabric, such as nylon, having a superior gas permeability. The shoulder belt 3 is fixedly sewn, at its proximal end, on the central portion of the belt body 2 at its upper edge, so that the shoulder belt 2 and the belt body 2 cooperate to represent an inversed T-shaped configuration, as shown in FIG. 1. A hook-and-loop fastener 3a, as a securing means, is fixed, for example, by means of sewing or adhesive, to the inner surface of the forward end portion of the shoulder belt 3. A pocket fabric 6 of an elastic material is sewn on the inner surface of the proximal portion of the shoulder belt 3, so as to form a pocket 7. A reinforcing plate 8 of a hard material, such as a plastic material, for example, is accommodated within the pocket 7. The reinforcing plate 8 controllably restricts inflation of the bag 4 to the breast portion of a user, as will be mentioned later.

The bag 4 may be a balloon of rubber, vinyl chloride, or polyethylene, for example. The bag 4 is received within the pocket 7 and disposed between the pocket fabric 6 and the reinforcing plate 8. The bag 4 includes a fluid supply conduit 9 which extends outwardly from the pocket 7. The fluid supply conduit 9 is provided with a check valve (not shown). The fluid supply conduit 9 of the bag 4 is adapted to be connected, for example, with a manually operated pump (not shown) and a pressure gauge(not shown), if necessary. Actuation of the manually operated pump while monitoring the pressure gauge causes fluid (including gels), such as air, water, or the like, to be filled into the bag 4 through the fluid supply conduit 9, so as to cause the bag 4 to be inflated.

Figure 4:
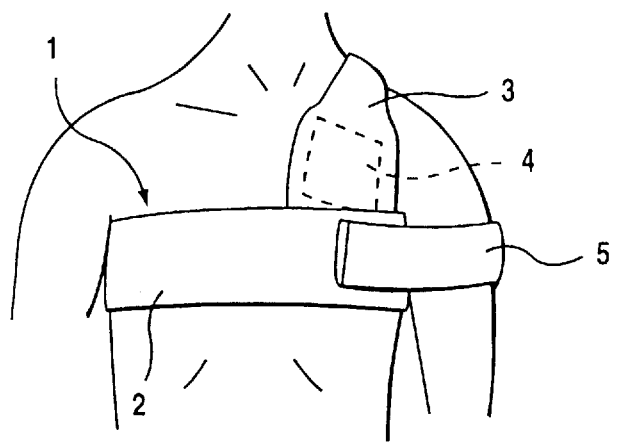
FIG. 4 is a front view showing the breast presser belt of the invention being wrapped around a breast portion of a user.
Figure 5:
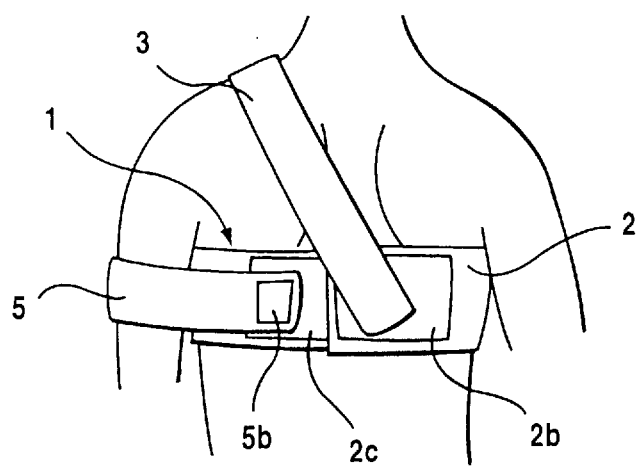
FIG. 5 is a rear view showing the breast presser belt of the invention being wrapped around the breast portion of the user.

The manner in which the breast presser belt 1 of the invention is wrapped around the breast portion of a user will be explained below with reference to FIGS. 4 and 5.

The belt body 2 is first wrapped around the breast portion of a user, by extending the belt body 2 around the breast portion from the breast side to the dorsum side (the back side), so that the hook-and-hoop fasteners 2a and 2c at the opposite ends of the belt body 2 are fastened together. Then, the shoulder belt 3 is extended from the breast side over the shoulder to the back side of a user, so that the hook-and-loop fastener 3a at the forward end portion of the shoulder belt 3 may be fastened to the hook-and-loop fastener 2b of the belt body 2.

When the wrapping operation of the breast is completed, the bag 4 is inflated. The inflation of the bag 4 is restricted to the breast portion by means of the reinforcing plate 8. Thus, the breast presser belt 1 pressurizes the breast portion and securely held against the breast portion. In this connection, it is noted that the amount of fluid to be filled within the bag 4 may be varied by the manually operated pump while monitoring the pressure gauge, depending upon a bodily shape of a user or patient, whereby pressurizing force may be desirably controlled so as to give an appropriate pressure to the patient. It is also noted that the controlled pressurizing force may be maintained for an extended period of time by means of the check valve. Furthermore, an automatic pressuring force control unit using a computer may be employed, if necessary, so as to control the pressure within the bag 4.

One embodiment of the invention has been explained in the above, it is noted, however, that the invention should not be limited to such embodiment which is solely given for the purpose of illustration. Rather, various modifications may be made on the basis of the gist of the invention.

In the above embodiment, the bag 4 is accommodated within the pocket 7 of the shoulder belt 3, so as to be securely attached to the shoulder belt 3. It is noted, however, that the bag 4 may be attached to the shoulder belt 3, for example, by means of hook-and-loop fasteners or double-sided adhesive tape. Alternatively, the bag 4 may be simply urged against the breast portion by means of the shoulder belt 3.

Figure 6:
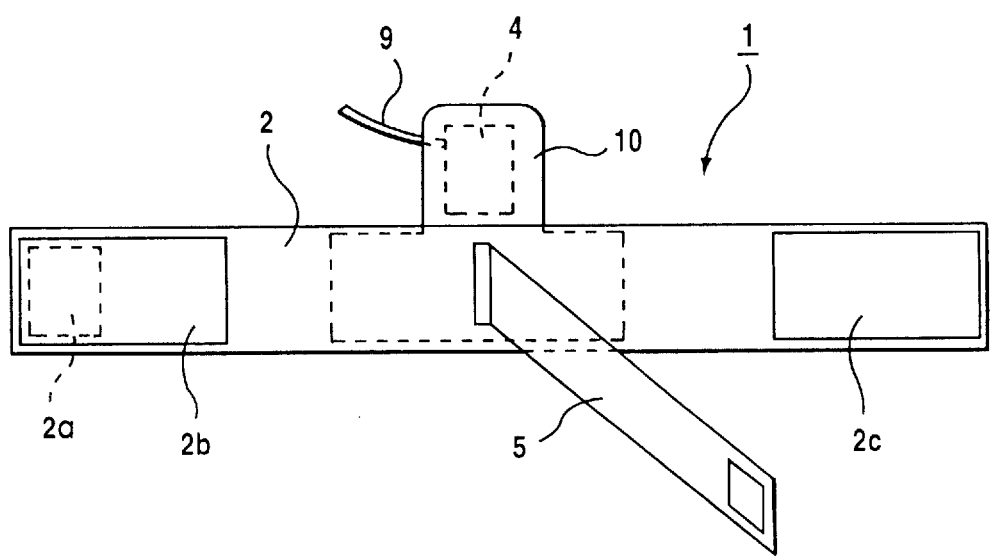
FIG. 6 is a front elevational view showing a breast presser belt according to another embodiment of the invention.

In the above embodiment, the shoulder belt 3 is employed, as a presser member, which passes over the shoulder so as to connect together the breast side and the back side of the belt body 2. It is noted, however, that, as shown in FIG. 6, a hard plate member 10 of an inversed T-shaped configuration (when viewed in FIG. 6) attached to the belt body 2 at predetermined position may be used as a presser member. The plate member 10 is formed from a hard material. In this case, the bag 4 may be attached directly to inner surface of the hard plate member 10, for example, by means of hook-and-loop fasteners or double-sided adhesive tape, so as to cause the bag 4 to be solely inflated inwardly of the hard plate member 10.

In the above embodiment, the belt body 2 is provided with the arm fixing belt 5 for fixing the left arm which is nearer to the portion to be pressed. It is noted, however, that the belt body 2 is not necessarily provided with the arm fixing belt 5, though it is preferable to provide the arm fixing belt 5 so as to cause the arm, which is nearer to the portion to be pressed, to be fixed at a position, in order to facilitate early healing of a wound.

In the above embodiment, the opposite end portions of the belt body 2 are fastened together at a position on the back side. It is noted, however, that the belt body 2 may be designed so as to cause the opposite end portions thereof to be fastened together at a position on the breast side.

In the above embodiment, the opposite end portions of the belt body 2, the forward end portion of the shoulder belt 3, and the forward end portion of the arm fixing belt 5 are appropriately fastened by means of the hook-and-loop fasteners 2a, 2b, 2c, 3, 5a and 5b. It is noted, however, that any means capable of fastening two members together, other than the hook-and-loop fasteners, may be used. For example, a pair of male and female hooks, buttons, a length of cord or the like may be used.

The breast presser belt of the invention may be used not only for pressuring an incision wound after operation of implanting a pacemaker, but also, for example, for performing hemostasis relative to a wound formed during catheter inspection or insertion of injection needles, or for maintaining a catheter at a fixed position during catheter inspection.

As mentioned above, and in accordance with the invention, a breast portion of a patient may be pressurized using inflation of the bag, so that the presser member for the bag and the belt body may be securely fastened to the breast portion. Thus, any shifting or displacement of the pressurized position is not caused, so that growing of tissue around the wound may be facilitated. Free activity of a patient may be also permitted, without requiring him or her of keeping still on a bed, since the breast portion of the patient may be securely pressurized by the invention. Furthermore, allergic poisoning due to the use of medical adhesive tape may be prevented. The invention may be applied to a female having larger breasts.

The breast side and the back side of the belt body is connected with each other by means of the shoulder belt passing over the shoulder of a patient Thus, the belt body may be prevented from being slipped downwardly by means of the shoulder belt. This allows a pressurized position to be maintained stably for an extended period of time.

The direction in which the bag may be inflated is restricted solely toward the breast side. Thus, a pressuring position may be effectively pressurized.

The arm which is nearer to the breast portion to be pressed may be fixed by the reinforcing member. Thus, healing of a wound may be facilitated.

It will further be obvious to those skilled in the art that many variations may be made in the above embodiments, here chosen for the purpose of illustrating the present invention, and full result may be had to the doctrine of equivalents without departing from the scope of the present invention, as defined by the appended claims.

We claim:

1. A breast presser belt for applying controlled pressure to an incision or wound of a user comprising a belt body adapted to be removably wrapped around a breast portion of a user, a shoulder belt extending perpendicular to and from the belt body over to the breast portion and connecting together a breast-side portion and a back-side portion of the belt body, a hard reinforcing plate attached to the inner side of the shoulder belt toward the breast portion, and an inflatable bag attached to the inner surface of the reinforcing plate and comprising inflation means; whereby the reinforcing plate controllably restricts inflation of the bag solely towards the breast portion of the user.

2. A breast presser belt for applying controlled pressure to an incision or wound of a user; comprising a belt body adapted to be removably wrapped around a breast portion of a user, a hard plate member of an inversed T-shaped configuration attached to the belt body, the hard plate member being formed from a hard material and having a portion extending perpendicularly from the belt body to a position over to the breast portion of a user during use, and a bag attached to the inner surface of the plate member at a predetermined position and comprising inflation means; whereby the reinforcing plate controllably restricts inflation of the bag solely towards the breast portion of the user.

3. The breast presser belt according to either one of claims 1 or 2, wherein an arm fixing belt is attached to the belt body at a predetermined position.

\* \* \* \* \*